(12) United States Patent
Ostermaier et al.

(10) Patent No.: US 6,599,398 B1
(45) Date of Patent: Jul. 29, 2003

(54) RECOVERY OF ADIPONITRILE FROM A MIXTURE OF ADIPONITRILE, AMINOCAPRONITRILE AND HEXAMETHYLENEDIAMINE

(75) Inventors: John Ostermaier, Wilmington, DE (US); Leon Scott, Wilmington, DE (US); James Hastings, Victoria, TX (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/197,882

(22) Filed: Jul. 17, 2002

(51) Int. Cl.⁷ .................. B01D 3/00; C07C 209/84; C07C 209/86; C07C 255/00
(52) U.S. Cl. .............. 203/74; 203/75; 203/77; 203/78; 203/80; 203/99; 203/DIG. 9; 203/DIG. 19; 564/497; 558/456
(58) Field of Search ............... 203/73, 74, 75, 203/77, 78.2, 80, 100, 99, DIG. 19, DIG. 9; 564/492, 498, 497; 558/459, 456

(56) References Cited

U.S. PATENT DOCUMENTS 5,961,788 A * 10/1999 Ostermaier ............ 203/37
6,139,693 A * 10/2000 Bassler et al. ........... 203/49
6,251,229 B1 * 6/2001 Luyken et al. ........... 203/91
6,462,220 B1 * 10/2002 Luyken et al. ........... 558/459

* cited by examiner

Primary Examiner—Virginia Manoharan
(74) Attorney, Agent, or Firm—Gerald E. Deitch

(57) ABSTRACT

Process for the recovery of a purified adiponitrile (ADN) from a mixture of adiponitrile, aminocapronitrile and hexamethylenediamine, utilizing two sequential distillations: (1) a first distillation in which the mixture is distilled in a distillation column at a head pressure that causes at least 7% of the ADN to go into the distillate, along with bishexamethylenetriamine (BHMT) and 2-cyanocyclopentylideneimine (CPI), and (2) a second distillation in which the distillate from the first distillation is distilled in a second distillation column at a head pressure sufficient to cause minimum-temperature azeotropy between ADN and BHMT, thereby allowing the majority of the BHMT and CPI to be removed from the second distillation as distillate, and ADN, substantially free of both BHMT and CPI, to be removed as bottoms.

4 Claims, 1 Drawing Sheet

RECOVERY OF ADIPONITRILE FROM A MIXTURE OF ADIPONITRILE, AMINOCAPRONITRILE AND HEXAMETHYLENEDIAMINE

BACKGROUND OF THE INVENTION

This invention relates to recovery of unreacted adiponitrile (ADN) in a mixture of ADN, aminocapronitrile (ACN) and hexamethylenediamine (HMD) that is formed by the partial hydrogenation of ADN. The ADN can come from the hydrocyanation of butadiene (BD), hydrodimerization of acrylonitrile, aminolysis of adipic acid or any other technique. It is known that ADN can by partially hydrogenated to HMD and ACN by reacting the ADN with hydrogen in the presence of a heterogeneous catalyst, notably iron or Raney cobalt. Such hydrogenations result in the production of undesirable by-products, including bishexamethylenetriamine (BHMT) and high boiling tars.

If such a process were to be run in a way that unreacted ADN is recycled back to the hydrogenation reactor, the BHMT would be recycled back with it and, as a result, the BHMT would be expected to increase over time, leading to an unacceptable level of accumulation in the system.

After the partial hydrogenation reaction, the resulting ACN and HMD need to be separated from the unreacted ADN and from each other. The separations can be effected using fractional distillation. During such distillation an undesirable byproduct, 2-cyanocyclopentylideneimine (CPI) results from the isomerization of ADN under alkaline conditions that exist during distillation.

One way to separate the CPI from the ADN is by simple, fractional distillation, in which the CPI is obtained as a distillate. However, such simple fractional distillation, if practiced using conventional operating conditions, i.e., less than 20 mm Hg head pressure, would not allow BHMT to be separated along with the CPI from the ADN.

SUMMARY OF THE INVENTION

The present invention provides a process in which BHMT and CPI can be separated together from ADN in a mixture comprising all three components.

In particular, the present invention is a process for recovering substantially pure ADN from a feed mixture comprising BHMT, ADN, CPI and high boiling tars, said process comprising the following sequential steps:

(1) distilling the mixture in an ADN Recovery Distillation Column having a head pressure in the range of 2 to 150 mm Hg to produce a substantially tar-free distillate comprising at least 70% of the ADN in the feed mixture, BHMT and CPI, and a bottoms product comprising substantially all of the tars and the remainder of the ADN in the feed mixture; and (2) redistilling the distillate from step (1) in an ADN Refining Distillation Column having a head pressure in the range of 20 to 150 mm Hg, which causes a minimum temperature azeotrope to form between ADN and BHMT, to produce (i) a distillate containing the majority of the BHMT and CPI present in the distillate from step (1), and (ii) an ADN bottoms product that is substantially free of both BHMT and CPI.

BRIEF DESCRIPTION OF THE DRAWING

The Drawing consists of one FIGURE showing a block diagram that illustrates the process of the present invention.

DETAILED DESCRIPTION OF THE INVENTION

Figure 1:
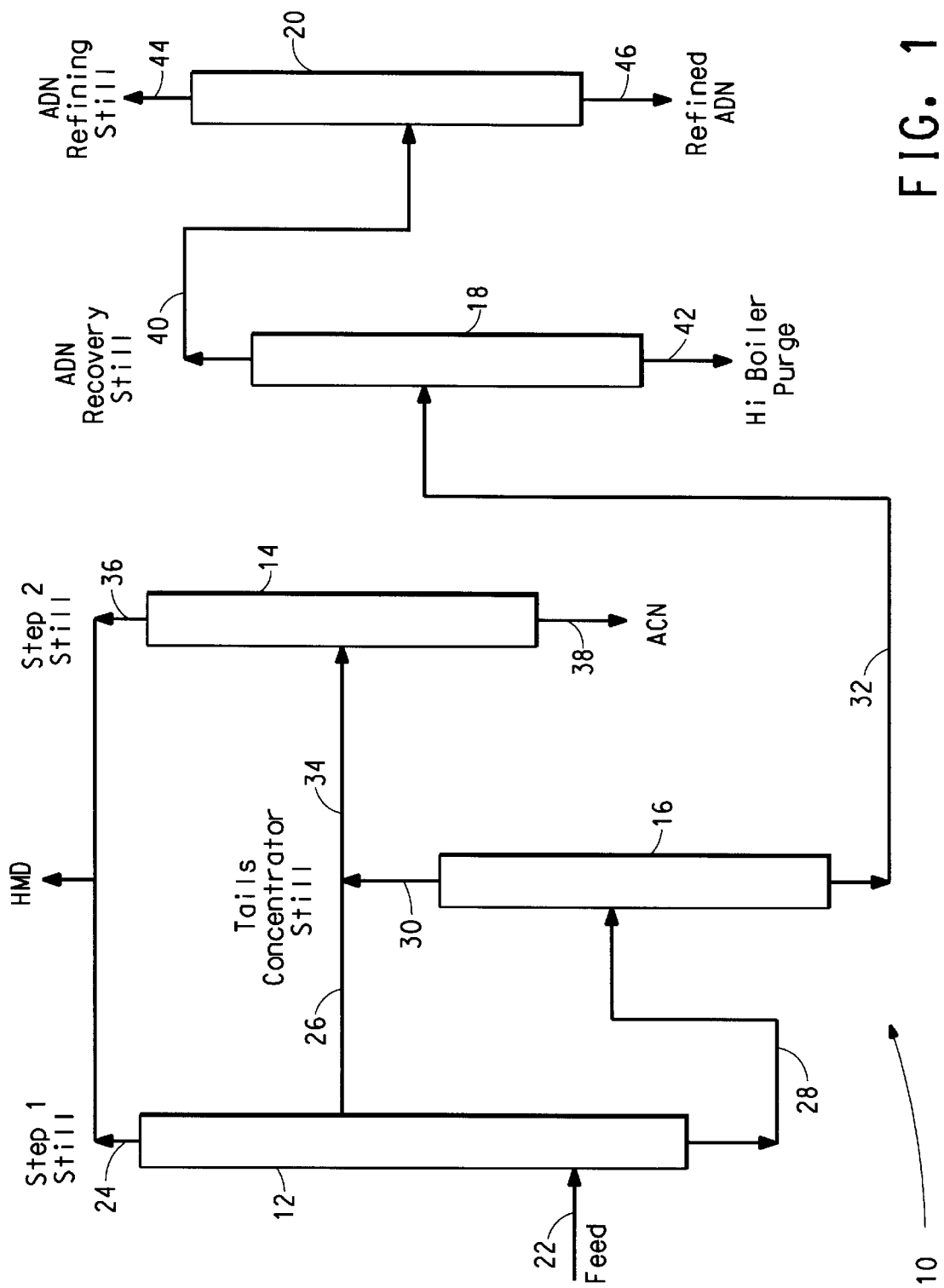

Referring now to the Drawing, a system 10 for separating CPI and BHMT together from ADN, comprises a step 1 distillation column 12, a step 2 distillation column 14, a tails concentrator distillation column 16, an ADN recovery still 18 and an ADN refining still 20.

A feed material 22 is the product of a partial hydrogenation of ADN and comprises ADN, HMD, ACN, high boiling tars, BHMT, tetrahydroazepine (THA), polarographically reducible impurities (PRI) and low boiling impurities.

The feed material 22 is introduced into the lower section of step 1 distillation column 12, preferably at the base. The column 12 is operated under conditions that cause most of the HMD and low boiling impurities to exit the column as distillate 24, the ACN to be removed with a small portion of the HMD as a side-draw 26 above the feed point, and the ADN and high boilers to be removed as a bottoms 28, along with a minor portion of the HMD and ACN. Typical column temperatures are in the range of 120 to 185 degrees C., with a typical head pressure of 70 mm Hg. Preferably column 12 is packed with structured packing. The column is operated with a reflux ratio of about 3.

The bottoms 28 of column 12 are fed to the tails concentrator still 16 and fed into still 16 at a feed point located near or at the middle of the column. The still 16 is operated under conditions that cause the HMD and ACN to be taken overhead as distillate 30, and the ADN and high boilers to be removed as bottoms 32. Typical column temperatures are in the range of 110 to 175 degrees C., with head pressure of about 13 mm Hg and reflux ration of about 1.0. The still 16 is packed with structured packing.

The distillate 30 is combined with the side-draw 26 to provide a stream 34 that is fed into the step 2 column 14. The stream 34 is introduced into column 14 at or near the middle of the column. The column is operated under conditions that cause the HMD to be recovered as distillate 36, and the ACN to be recovered as a bottoms 38. Typical column temperatures are in the range of 145 to 180 degrees C., with a head pressure of about 150 mm Hg, with a reflux ratio of about 2.5. The column 14 is packed with structured packing. Preferably, column 14 is operated with a sigmoidal temperature profile as described in U.S. Pat. No. 6,248,926, issued to Ostermaier and Scott on Jun. 19, 2001. Such sigmoidal temperature profile allows the THA to be removed along with the ACN in the bottoms 38.

The bottoms 32 are fed into the ADN recovery still 18 at a feed point located somewhere below the midpoint of the column. The still 18 is operated under conditions to produce a substantially tar-free distillate 40 comprising at least 70% of the ADN in the feed mixture 32, together with the BHMT and CPI in the feed mixture 32. The bottoms 42 will comprise substantially all of the tars and the remainder of the ADN in the stream 32. Typical head pressures are in the range of 2 to 150 mm Hg, with reflux of about 1.0. Still 18 contains a structured packing.

The distillate 40 is fed into the ADN refining still 20 at a feed point located above the column midpoint. The still 20 is operated with a head pressure in the range of 20 to 150 mm Hg and a reflux ratio of about 10. This causes a minimum temperature azeotrope to form between ADN and BHMT, to produce (i) a distillate 44 containing the majority of the BHMT and CPI present in. the distillate 40, and (ii) an ADN bottoms product 46 that is substantially free of both BHMT and CPI.

EXAMPLE

The process of the present invention was performed in a step-wise fashion (as opposed to a continuous, integrated operation) to evaluate the ability of the process to produce refined streams of HMD, ACN and ADN. Drawing reference numerals are shown in parentheses. All percentages are by weight. The designation "ND" in the tables means not detectable. The expressions "still" and "distillation column" are used interchangeably throughout the specification and drawing.

The feed material (22) was made by blending crude HMD with refined ACN and refined ADN. The composition of the feed was nominally 40% HMD, 40% ACN, and 20% ADN. Impurities consisted of the normal distribution of impurities present in crude HMD (hexamehtyleneimine (HMI), diaminocyclohexane (DCH), BHMT, etc). Air was sparged through the feed mixture to produce about 300 ppm THA in the feed.

All distillation columns (stills) consisted of 2 inch diameter vacuum jacketed sections containing Sulzer BX wire mesh packing, which has a height equivalent of a theoretical plate of 6 inches. All reboilers were electrically heated thermosyphon reboilers, which give low hold up times Samples taken from the stills were analyzed by gas chromatography. Compositions were determined by area % (no internal standards were used). THA analysis was done by polarography.

The purpose of the Step 1 column (12) is to take most of the HMD and the low boilers overhead, obtain a side draw that is enriched in ACN, and a bottoms draw that contains the ADN and high boilers. The column was operated to keep the ACN content of the distillate below 1000 ppm and the ADN content of the side draw below 100 ppm.

The column configuration consisted of 10 feet of packing above the reboiler, at which point the side draw was located, above which was placed 12.5 feet of packing. This gives a total of about 45 theoretical stages in the column. There was a reflux splitter at the top of the column, as well as a heated water condenser followed by a cold water condenser to remove any low boilers that might pass through the warm condenser. The feed was preheated to 100 degrees C. prior to entering the column.

The column was operated at 70 mm Hg head pressure, and the pressure drop in the column was 13 mm Hg. Reflux ratio was nominally 3. The desired composition profile in the column was maintained by controlling the temperature in the column 7.5 feet below the condenser by adjusting the distillate flow rate. The head temperature was 119.5 degrees C., and the control point temperature was 130 degrees C. The ADN concentration of the side draw was controlled by varying the side draw rate to maintain the temperature 5 feet from the bottom of the column at 150 degrees C. The bottoms temperature was 185 degrees C.

Analysis of the streams associated with Step 1 column operation were as follows:

|  | Feed (22) | Distillate (24) | Side (26) | Bottoms (28) |
| --- | --- | --- | --- | --- |
| ppm THA | 298 | 100 to 300 | 800 | <100 |
| ppm PRI | 175 to 240 | 1050 | 1120 to 1714 |  |
| % HMD | 39.8 | >98 | 14 | 3.0 |
| % ACN | 39.3 | 0.04 to 0.06 | 86 | 12 |
| % ADN | 19.7 | ND | <100 | 82 |
| ppm CPI | 21 | ND | ND | 212 +/− 85 |
| % BHMT | 0.20 | ND | ND | 0.7 to 1.4 |

The purpose of the Step 2 column (14) is to take the side draw from the Step 1 column (26) and separate it into HMD distillate with less than 1000 ppm ACN, and an ACN bottoms stream which contains less than 100 ppm HMD. The same column configuration was used here as for the Step 1 column, except that no side draw was taken.

The Step 2 column run was made at a head pressures of 150 mm Hg. Column pressure drop was 18 mm Hg. The column was fed 10 feet above the reboiler, which gave 12.5 feet of packing (25 theoretical stages) in the rectifying section, and 10 feet of packing (20 theoretical stages) in the stripping section. The reflux ratio was between 1.8 and 3.2. The composition profile was established by adjusting the distillate rate to control the temperature 7.5 feet below the condenser.

In this run, the column temperatures were 147 degrees C. at the condenser, 162 degrees C. at the control point, and 179 degrees C. in the reboiler. Stream analyses were as follows:

|  | Feed (34) | Distillate (36) | Bottoms (38) |
| --- | --- | --- | --- |
| ppm THA | 796 | 50 to 70 | 900 |
| ppm PRI |  | 30 |  |
| % HMD | 13.3 | >98 | 100 ppm |
| % ACN | 86.3 | 450 to 550 ppm | >99 |
| % ADN | 0.118 | ND | 0.135 |
| ppm CPI | ND | ND | ND |
| % BHMT | ND | ND | ND |

(Note: The presence of ADN in the feed and bottoms for this step was caused by an upset in Step 1 which put some ADN into the side draw.)

The purpose of the Tails Concentrator (16) is to take the bottoms from the Step 1 Column (28) and recover the HMD and ACN as distillate (30), while obtaining a bottoms stream (32) that contains the ADN, BHMT, and tars. This column must be operated at high vacuum to keep the base temperature as low as feasible to minimize CPI formation.

The column consisted of 5 feet of Sulzer packing below the feed point, and 5 feet above. The reboiler was again a themosyphon type with electrical heating. The feed was preheated to 100 degrees C. The hold up time in the reboiler was estimated at 10 to 15 minutes.

The column was operated at a head pressure of 13.5 mm Hg, and a pressure drop of 8 mm Hg. The reflux ratio was initially 1.7 and was reduced to 1.0 over the course of the run. The product stream compositions were maintained by varying the distillate rate to control the temperature at the feed point. During operation the condenser temperature was 109 degrees C., the control temperature was 126 degrees C., and the bottoms temperature was 175 degrees C. Stream analyses were as follows:

|  | Feed (28) | Distillate (30) | Bottoms (32) |
|---|---|---|---|
| ppm THA | 47 | 380 to 450 | ND |
| % HMD | 3.0 | 19 | 35 ppm |
| % ACN | 13.6 | 81 | 500–1500 ppm |
| % ADN | 81.0 | <50 ppm | 97.5 |
| ppm CPI | 202 | ND | 265 +/− 42 |
| % BHMT | 1.0 | ND | 1.1 |

Note that the amount of CPI in the tails is quite low, which is highly desirable. Also, note the apparent generation of THA in this step, possibly from the break up of higher boiling forms of PRI.

The purpose of the ADN Recovery Column (18) is to take the bottoms from the Tails Concentrator Column (16) and recover the ADN as distillate (40), while purging tars as a bottoms stream (42). This column must be operated at high vacuum to keep the base temperature as low as feasible to minimize CPI formation.

The column consisted of 2.5 feet of Sulzer packing below the feed point, and 7.5 feet above. The reboiler was again a themosyphon type with electrical heating. The feed was preheated to 100 degrees C. The hold up time in the reboiler was estimated at 100 to 150 minutes.

The column was operated at a head pressure of 13.5 mm Hg, and a pressure drop of 10 mm Hg. The reflux ratio was 0.85. The bottoms draw rate was adjusted to control the CPI level in the ADN distillate below 1000 ppm. During operation the condenser temperature was 160 degrees C., and the bottoms temperature was 176 degrees C. Stream analyses were as follows:

|  | Feed (32) | Distillate (40) | Bottoms (42) |
|---|---|---|---|
| ppm THA | 41 | ND |  |
| % HMD | 35 ppm | 0.09 | ND |
| % ACN | 0.2 | 0.41 | ND |
| % ADN | 97.1 | 98.6 | 95 |
| ppm CPI | 248 | 830 | 440 |
| % BHMT | 1.02 | 0.79 | 0.98 |
| Tars |  |  | 4.57 |

In order to keep the CPI level of the distillate below 1000 ppm, it was necessary to take a 20% bottoms purge, which corresponds to an overall process ADN yield loss of 4%. This large a yield loss would probably justify the use of a high vacuum flasher to recover some of the ADN contained in the ADN Recovery column tails.

Two things should be noted from this run. First, there is virtually no separation of BHMT in this column. Second, the amount of CPI in the recovered ADN can be kept below 1000 ppm by controlling the bottoms draw. It should be noted that when the hold-up time (HUT) in the reboiler was reduced from 150 to 100 minutes, the CPI content of the distillate was reduced from 750 to 375 ppm. This indicates that by minimizing the HUT in the reboiler, it should be possible to considerably reduce the amount of CPI generation experienced in this step. Preferably, the column should be operated between head pressures of 2 and 150 mm Hg. A head pressure of 2 mm Hg or higher should avoid the need for excessive column diameters. A head pressure of 150 mm Hg or lower should avoid the generation of high column temperatures that can cause the decomposition of ADN.

The purpose of the ADN Refining Column (20) is to remove as distillate the CPI and BHMT contained in the ADN Recovery Column distillate (40) and obtain ADN with less than 50 ppm CPI as bottoms product (46). Initially the ADN was recovered as a side draw just above the reboiler with no bottoms draw, but it was noted that this mode of operation caused high levels of CPI (greater than 50 ppm) in the ADN product, so a switch was made to bottoms draw. This dropped the CPI content of the refined ADN to less than 50 ppm. Apparently, side draw operation led to the accumulation of high boilers in the bottoms, which in turn caused the rate of CPI generation in the bottoms to increase. Taking a bottoms draw prevented the accumulation of high boilers and reduced the rate of CPI generation. Since the bottoms draw was a better way to operate, all of the data reported are for bottoms draw operation.

The column consisted of 5 feet of Sulzer packing above the feed point, and 15 feet of packing below the feed point. This corresponds to about 22 theoretical stages, allowing for the poor efficiency caused by poor wetting of the packing. The reboiler was a thermosyphon type with electrical heating. The feed (40) was preheated to 100 degrees C., and the HUT in the reboiler was about 20 minutes.

The column was operated at a head pressure of 80 mm Hg. The reflux ratio was 13. The column was operated at this pressure in order to form a low boiling azeotrope between BHMT and ADN, which caused most of the BHMT to purge with the CPI. The distillate rate was adjusted to control the CPI in the bottoms product. The condenser temperature was 213 degrees C., and the reboiler temperature was 215 degrees C. Stream analyses were as follows:

|  | Feed (40) | Distillate (44) | Bottoms (46) |
|---|---|---|---|
| % ADN | 98.6 | 89.9 | >99 |
| ppm CPI | 830 | 11,000 | 37 +/− 10 |
| % BHMT | 0.96 | 6.7 | 0.21 |

The feed material (40) was made up to approximate the distillate material (40) from the ADN Recovery Column (18), with a slightly higher percentage (by weight) of BHMT, as indicated in the table above.

There are two significant conclusions that can be drawn from the ADN Refining Column data. First, ADN Recovery was 92% for this step. Second, by operating at a head pressure of 80 mm Hg, a low boiling azeotrope was formed between BHMT and ADN, allowing the BHMT to be purged from the system as distillate. Isobaric ebulliometric measurements at two pressures (10 and 20 mm Hg) were used to develop vapor-liquid equilibrium data for the BHMT/ADN binary pair. This data indicated that a low boiling azeotrope develops above a pressure of 20 mm Hg. This indicates that head pressures as low as 20 mm Hg may be used. Head pressures above 150 mm Hg are impractical because of decompositions caused by resulting high column temperatures.

The foregoing example is offered as illustrative only. The invention is defined by the claims below, in which column names are used to identify and differentiate one column from the others.

What we claim:

1. A process for recovering a purified adiponitrile (ADN) from a feed mixture comprising bishexamethylenetriamine (BHMT), ADN, 2-cyanocyclopentylideneimine (CPI), and high boiling tars, said process comprising the following sequential steps:

(1) distilling the mixture in an ADN Recovery Distillation Column having a head pressure in the range of 2 to 150 mm Hg to produce a substantially tar-free distillate comprising at least 70% of the ADN in the feed mixture, BHMT and CPI, and a bottoms product comprising substantially all of the tars and the remainder of the ADN in the feed mixture; and then (2) distilling the distillate from step (1) in an ADN Refining Distillation Column having a head pressure in the range of 20 to 150 mm Hg, which causes minimum-temperature azeotropy between ADN and BHMT, thereby allowing the removal from the ADN Refining Distillation Column of (i) a distillate containing the majority of the BHMT and CPI present in the distillate from step (1), and (ii) a bottoms product that comprises ADN that is substantially free of both BHMT and CPI.

2. The process of claim 1, wherein the feed mixture to the ADN Recovery Distillation Column is the bottoms of a Tails Concentrator Distillation Column whose feed material is the bottoms of a Step 1 Distillation Column whose feed material is an ADN hydrogenation product comprising ADN, HMD, ACN, BHMT, tetrahydroazepine (THA), polarographically reducible impurities (PRI), and tars.

3. The process of claim 2, wherein a side draw from the Step 1 Distillation Column is combined with the distillate of the Tails Concentrator Distillation Column and fed to a Step 2 Distillation Column whose bottoms comprises ACN.

4. The process of claims 1, 2 or 3, wherein the head pressure of the ADN Recovery Column is 13.5 mm Hg, and the head pressure of the ADN Refining Distillation Column is 80 mm Hg.

\* \* \* \* \*

UNITED STATES PATENT AND TRADEMARK OFFICE
CERTIFICATE OF CORRECTION

PATENT NO.    : 6,599,398 B1                                              Page 1 of 1
DATED         : July 29, 2003
INVENTOR(S)   : Ostermaier et al.

It is certified that error appears in the above-identified patent and that said Letters Patent is hereby corrected as shown below:

Column 4,
Line 6, dealing with "% ADN", the entry "<100" should read -- <100 ppm --.

Signed and Sealed this

Fourteenth Day of October, 2003

JAMES E. ROGAN
*Director of the United States Patent and Trademark Office*